United States Patent
Gross et al.

(10) Patent No.: US 9,579,640 B2
(45) Date of Patent: Feb. 28, 2017

(54) AMIDINATE AND GUANIDINATE COMPLEXES, THEIR USE AS CHAIN TRANSFER POLYMERIZATION CATALYSTS AND LONG CHAIN ALCOHOLS OBTAINED BY SUCH PROCESS

(71) Applicant: SASOL OLEFINS & SURFACTANTS GMBH, Hamburg (DE)

(72) Inventors: Thoralf Gross, Brunsbuttel (DE); Holger Ziehe, Itzehoe (DE); Rhett Kempe, Bayreuth (DE); Winfried Kretschmer, Bayreuth (DE); Christian Hubner, Bayreuth (DE)

(73) Assignee: Sasol Performance Chemicals GmbH, Hamburg (DE)

( * ) Notice: Subject to any disclaimer, the term of this patent is extended or adjusted under 35 U.S.C. 154(b) by 0 days.

(21) Appl. No.: 14/405,505

(22) PCT Filed: Jun. 3, 2013

(86) PCT No.: PCT/EP2013/001614
§ 371 (c)(1),
(2) Date: Dec. 4, 2014

(87) PCT Pub. No.: WO2013/182290
PCT Pub. Date: Dec. 12, 2013

(65) Prior Publication Data
US 2015/0148505 A1 May 28, 2015

(30) Foreign Application Priority Data
Jun. 4, 2012 (EP) ..................... 12004263

(51) Int. Cl.
| | |
|---|---|
| *C08F 4/52* | (2006.01) |
| *C08F 4/10* | (2006.01) |
| *C08F 4/64* | (2006.01) |
| *C08F 4/76* | (2006.01) |
| *B01J 31/22* | (2006.01) |
| *B01J 31/12* | (2006.01) |
| *B01J 31/14* | (2006.01) |
| *B01J 31/18* | (2006.01) |
| *C07C 2/32* | (2006.01) |
| *C07C 11/02* | (2006.01) |
| *C07C 31/20* | (2006.01) |
| *C07F 7/00* | (2006.01) |
| *C07F 7/28* | (2006.01) |
| *C08F 110/02* | (2006.01) |

(52) U.S. Cl.
CPC ......... *B01J 31/2295* (2013.01); *B01J 31/122* (2013.01); *B01J 31/143* (2013.01); *B01J 31/1805* (2013.01); *C07C 2/32* (2013.01); *C07C 11/02* (2013.01); *C07C 31/202* (2013.01); *C07C 31/205* (2013.01); *C07F 7/006* (2013.01); *C07F 7/28* (2013.01); *C08F 110/02* (2013.01); *B01J 2231/122* (2013.01); *B01J 2231/46* (2013.01); *B01J 2231/70* (2013.01); *B01J 2231/766* (2013.01); *B01J 2531/007* (2013.01); *B01J 2531/46* (2013.01); *B01J 2531/48* (2013.01); *B01J 2531/49* (2013.01); *C07C 2531/22* (2013.01); *C08F 4/52* (2013.01)

(58) Field of Classification Search
CPC .......... C08F 4/50; C08F 4/52; C08F 4/60044; C08F 8/06; C08F 2810/40
See application file for complete search history.

(56) References Cited

U.S. PATENT DOCUMENTS

| | | | | |
|---|---|---|---|---|
| 5,043,515 | A * | 8/1991 | Slaugh | B01J 31/143 502/117 |
| 5,502,128 | A * | 3/1996 | Flores | B01J 31/1805 502/349 |
| 5,777,120 | A | 7/1998 | Jordan et al. | |
| 7,589,150 | B2 * | 9/2009 | Hanna et al. | 525/64 |
| 7,718,834 | B2 * | 5/2010 | Ziehe | C07C 29/54 568/851 |
| 2010/0209610 | A1 * | 8/2010 | Cameron | C07F 7/006 427/255.28 |
| 2013/0131294 | A1 * | 5/2013 | Hagadorn | C08F 210/16 526/170 |

FOREIGN PATENT DOCUMENTS

| | | |
|---|---|---|
| CN | 102432700 | 5/2012 |
| EP | 0329891 | 8/1989 |
| GB | 1309469 | 3/1973 |
| WO | WO97/45434 | 12/1997 |

OTHER PUBLICATIONS

Zhou et al. Inorg. Chem. Commun. 2007, 10, 1262-1264.*
Aldrich Catalog 1994-1995, p. 1066.*
Collins, S. Coord. Chem. Rev. 2011, 255, 118-138.*
Kretschmer, W.P.; Bauer, T.; Hessen, B.; Kempe, R. Dalton Trans. 2010, 39, 6847-6852.*
Zhou, M.; Tong, H., Wei, X.; Liu, D. J. Organomet. Chem. 2007, 692, 5195-5202.*
Otten, E.; Dijkstra, P.; Visser, C.; Meetsma, A.; Hessen, B. Organometallics 2005, 24, 4374-4386.*
Hersk-Korine, "Bis(Trimethylsilyl)benzamidinate . . . " J. Organometallic Chem, vol. 503, Nov. 1995, p. 307-314.
Liguori et al. "Titanium Monoamadinate . . . " Macromolecules, vol. 36, Jul. 2003, p. 5451-5458.

(Continued)

*Primary Examiner* — Rip A Lee
(74) *Attorney, Agent, or Firm* — Bushman Werner, P.C.

(57) ABSTRACT

The present invention is concerned with a catalyst composition comprising titanium-, zirconium- and/or hafnium amidinate complexes and/or titanium-, zirconium- and/or hafnium guanidinate complexes and organo aluminium and/or organic zinc compounds, a coordinative chain transfer polymerization (CCTP) process employing the catalyst composition as well as long chain aluminium alkyls and subsequent alcohols obtained by such process.

21 Claims, No Drawings

(56) References Cited

OTHER PUBLICATIONS

Zhou et al. "Syntheses and Structures of Non-Symmetric Guanidinato . . . " J. Organometallic Chem, vol. 692, Oct. 2007, p. 5195-5202.
Zhou et al. "Sythesis, Structure, and Catalytic Properties . . . " Inorg. Chem. Comm., vol. 10, Oct. 2007, p. 1262-1264.
Collins, "Polymerization Catalysis with Transition Metal . . . " Coord. Chem. Rev., vol. 255, Jan. 2011, p. 118-138.
Kretschmer, et al. "Reversible Chain Transfer . . . " Chem. Eur. J., vol. 12, 2006, p. 8969-8978.
Amin, et al. "Versatile Pathways for In Situ Polyolefin . . . " Angew. Chem., vol. 120, 2008, p. 2006-2025.
Bialek "Effect of Catalyst Composition . . . " J. Polym. Sci., vol. 48, 2010, p. 3209-3214.
Kretschmer, et al. "An efficient yttrium catalysed version . . . " Dalton Trans., vol. 39, 2010, p. 6847-6852.
Kretschmer, et al. "Highly active/selective and adjustable zirconium . . . " J. Organomet. Chem., vol. 692, 2007, p. 4569-4579.
Haas, et al. "Synthesis of Alumina-Terminated Linear PE . . . " Organometallics. vol. 30, 2011, p. 4854-4861.
Zinck, et al. "Coordinative Chain Transfer Polymerization" Chem. Rev., 2013, DOI: dx.doi.org/10.1021/cr300289z.
Zhiyun, Li, Synthesis and Characterization of High Molecular Weight Hydroxy Terminated . . . , Institute of Polymer Science, Sun Yat-sen Univ, 2010, p. 44-45.

\* cited by examiner

AMIDINATE AND GUANIDINATE COMPLEXES, THEIR USE AS CHAIN TRANSFER POLYMERIZATION CATALYSTS AND LONG CHAIN ALCOHOLS OBTAINED BY SUCH PROCESS

CROSS REFERENCE TO RELATED APPLICATION

This application is a U.S. National Phase of PCT/EP2013/001614, filed on Jun. 3, 2013, which claims priority to European Application EP12004263.5, filed Jun. 4, 2012, the disclosures of which are incorporated herein by reference for all purposes.

FIELD OF THE INVENTION

The present invention relates to a catalyst composition comprising titanium-, zirconium- and/or hafnium amidinate complexes and/or titanium-, zirconium- and/or hafnium guanidinate complexes and organo aluminium and/or organo zinc compounds, a coordinative chain transfer polymerization (CCTP) process employing the catalyst composition as well as long chain aluminium alkyls and subsequent alcohols obtained by such process.

BACKGROUND OF THE INVENTION

The polymerization of olefins with the use of Ziegler-Natta catalysts is an established technique known since the early 1950s and is widely applied in industry. Ziegler-Natta catalysts are based on transition metal compounds, especially titanium and organoaluminium compounds. Numerous metal complexes have been described in the literature as catalysts for olefin polymerization, among the publications are literature references teaching amidinate and guanidinate metal complexes and their use as polymerization catalysts such as WO 97/45434, U.S. Pat. Nos. 5,777,120 and 5,502,128. Bis(trimethylsilyl)benzamidinate zirconium dichlorides are taught by D. Herskovics-Korine in JOURNAL OF ORGANOMETALLIC CHEMISTRY, vol. 503, no. 2, 15 Nov. 1995, pages 307-314 as active catalysts in presence of a co-catalyst (methylaluminoxane, MAO) for polyethylene (PE) production. The use of Titanium monoamidinate-MAO catalysts for the polymerization of propene, styrene, and 1,3-butadiene is taught by Liguori et al. in MACRO-MOLECULES, vol. 36, no. 15, 1 Jul. 2003, pages 5451-5458. M. Zhou et al. in JOURNAL OF ORGANOMETALLIC CHEMISTRY, vol. 692, no. 23, 6 Oct. 2007, pages 5195-5202 teach the use of tris guanidinato zirconium and hafnium complexes as catalysts for PE production in presence of a co-catalyst MAO or $Et_2AlCl$. A further publication of M. Zhou et al. in INORGANIC CHEMISTRY COMMUNICATIONS, vol. 10, no. 11, 18 Oct. 2007, pages 1262-1264 relates to the synthesis and structure of non-symmetric zirconium guanidinato dimer complexes and their use in PE production in combination with MAO, MMAO (modified MAO) and $Et_2AlCl$. A review by S. Collins of different amidinate and guanidate catalysts and their use as polymerization catalysts is published in COORDINATION CHEMISTRY REVIEWS, vol. 255, no. 1-2, 1 Jan. 2011, pages 118-138. None of the above references is concerned with CCTP yielding oligomers of relatively low molecular weight and allowing the production of long chain alcohols or alpha olefins. Moreover, none of the catalyst systems is capable of producing Al-terminated oligomers.

A great variety of catalysts capable of catalyzing coordinative chain transfer polymerization (CCTP) has been proposed in the literature. CCTP is commonly used to control and modify molecular weights of polymers. These transition metal based catalysts are typically used together with co-catalysts which usually act as chain transfer agents. Suitable co-catalysts include alkyl zinc, alkyl aluminium, alkyl aluminium halides and alkyl alumoxanes, commonly used together with inert, non-coordinating ion forming compounds (activator), Lewis and Brönstedt acids and mixtures thereof. Such prior art processes are disclosed in W. P. Kretschmer et al.; Chem. Eur. J. 2006, 12, 8969-8978 and S. B. Amin, T. J. Marks; Angew. Chem. 2008, 120, 2034-2054 and Zinck et al.; Chem. Rev. 2013; DOI: dx.doi.org/10.1021/cr300289z.

One characteristics of CCTP is that polymer chains are end-capped with the respective main group metal of the co-catalyst and can be further functionalized (M. Bialek, J. Polym. Sci.: Part A: Polym. Chem. 2010, 48, 3209-3214 and W. P. et al., Dalton Trans. 2010, 39, 6847-6852).

CCTP typically requires the use of a metal complex as catalyst, a co-catalyst and optionally an activator. In the understanding of the present invention the co-catalyst is a chain transfer agent and may optionally but not necessarily be an activator at the same time. The activator may be for example a compound different from the chain transfer agent and not functioning as a chain transfer agent. Such activator in the understanding of the invention is under above circumstances not called a co-catalyst and only an activator.

Catalyst systems used in CCTP are often prone to ligand transfer from the catalyst onto the co-catalyst which results in a decreased activity (W. P. Kretschmer, B. Hessen, A. Noor, N. M. Scott, R. J. Kempe, Organomet. Chem. 2007, 692, 4569-4579). Especially, at high co-catalyst to catalyst ratios the catalyst activity is remarkably decreased. Hence, all known catalyst systems suffer from un-wanted olefin production due to β-hydride elimination. It is therefore an objective of the present invention to provide highly active catalysts showing only minor β-hydrid elimination and accordingly less side products (I. Haas, W. P. Kretschmer, R. Kempe, Organometalics 2011, 30, 4854-4861). Besides the total chain transfer efficiency should be close to 100%. In addition the catalyst should be capable of operating at high co-catalyst to catalyst ratios thereby suppressing β-hydrid elimination in view of the fact that the co-catalyst acts as chain transfer agent.

EP 0329891 A2 for instance discloses certain low molecular weight polyethylene alcohols having an average chain length of from about 20 to about 500 carbon atoms and a polydispersity of 1.04 to 1.20 and their conversion to end-functionalized polymers by introducing a functional group which replaces the hydroxyl group of the alcohol. The following functional groups are taught: halogen, alkanolamine, carboxyl, thiol, amine, quaternized amine radical, amide, quaternized dialkylamine, amine oxide, silyl and others.

The object of the present invention is to find stable highly active and selective metal complexes which are capable of polymerizing or co-polymerizing olefins and to finally transfer the produced carbon chain onto a co-catalyst. The co-catalyst thereby acts as a chain transfer agent and is functionalized with the carbon chain after the transfer. Subsequent to the transfer the obtained molecules can be derivatized via oxidation and hydrolyzation to yield functionalized carbon chains, in particular hydroxy terminated carbon chains. A further objective of the present invention is to provide a catalyst which can be prepared in an easy and economical fashion.

SUMMARY OF THE INVENTION

The present invention is defined by the independent claims. Preferred embodiments are disclosed in the subordinate claims or described hereunder.

The amidinate and guanidinate based metal complexes of this invention offer high stability. Moreover, the catalysts do not undergo ligand transfer from the catalyst onto the Al-atom and suppress efficiently β-hydrid elimination to overcome un-wanted side-products like olefins. In addition, the complexes differ significantly from previously disclosed complexes both structurally and in catalytic performance producing long chain carbons with narrow molecular weight distributions. The CCTP comprises a chain transfer of the alky group onto an aluminium atom and finally allows obtaining for instance after elimination pure alpha-olefins or after oxidation and hydrolysis alcohols. Hence, a method is provided which allows for the production of medium to long chain aluminium alkyls or finally alpha-olefins or alcohols.

DETAILED DESCRIPTION OF THE INVENTION

Hereinafter the components of the catalyst system are described in detail:
1. Metal-complex Comprising One of the Following Ligands:
1.1 Guanidinates

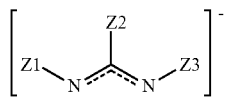

I with
$Z2=NR1R2$,
R1 and R2 are independently from each other hydrocarbon moieties, in particular C1 to C40, preferably C1 to C18, optionally substituted hydrocarbon moieties additionally comprising (not directly adjacent to the N-Atom) one or more nitrogen, oxygen, and/or silicon atom(s), further optionally linked with each other or with Z1 and/or Z3.
Z1 and Z3 independently from each other are:
  hydrocarbon moieties, in particular C1 to C40, preferably C3 to C22, most preferably C8 to C18 or more preferably C10 to C22, optionally linked with each other or with Z2, Z1 and Z3 optionally additionally comprising one or more nitrogen, oxygen, and/or silicon atom(s) (not directly adjacent to the N-Atom);
  preferably alkyl, in particular C1 to C40, preferably C3 to C22, most preferably C8 to C18, or aryl moieties, in particular C6 to C22, most preferably C8 to C18, optionally further substituted by hydrocarbyl groups, in particular C1 to C12, preferably C2 to C6, in particular alkyl, alkenyl or aryl groups, Z1 and Z3 optionally additionally comprising one or more nitrogen, oxygen and/or silicon atom(s) (not directly adjacent to the N-Atom); and
  substituted phenyl, in particular tolyl, in particular substituted in the 2 and/or 6 position,
    mono- or di- or tri-isopropyl phenyl, in particular 2,6-di-isopropyl phenyl,
    mono- or di- or tri-t-butyl phenyl, in particular 2,6 di-t-butyl phenyl,
    mono- or di- or tri-(C1 to C4)alkoxy phenyl, in particular 2,6-di-(C1 to C4)alkoxy phenyl, or
    mono- or or di-(C1 to C4)alkylamino phenyl, in particular 2,6-di-(C1 to C4) alkylamino phenyl.
and/or
1.2 Amidinates

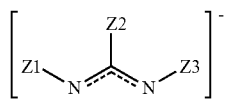

II with
Z1, Z2 and Z3 are independently from each other
  hydrocarbon moieties, in particular C1 to C40, preferably C3 to C22, most preferably C8 to C18, optionally linked with each other or with Z2, Z1 and Z3 optionally additionally comprising one or more nitrogen, oxygen, and/or silicon atom(s) (not directly adjacent to the N-Atom);
  preferably alkyl, in particular C1 to C40, preferably C3 to C22, most preferably C8 to C18, or aryl moieties, in particular C6 to C22, most preferably C8 to C18, optionally further substituted by hydrocarbyl groups, in particular C1 to C12, preferably C2 to C6, in particular alkyl, alkenyl or aryl groups, Z1 and Z3 optionally additionally comprising one or more nitrogen, oxygen and/or silicon atom(s) (not directly adjacent to the N-Atom for Z1 and Z3 and not directly adjacent the C-atom for Z2); and
  most preferably phenyl,
    substituted phenyl, in particular tolyl, in particular substituted in the 2 and/or 6 position,
    mono- or di- or tri-isopropyl phenyl, in particular 2,6-di-isopropyl phenyl,
    mono- or di- or tri-t-butyl phenyl, in particular 2,6 di-t-butyl phenyl,
    mono- or di- or tri-(C1 to C4)alkoxy phenyl, in particular 2,6-di-(C1 to C4)alkoxy phenyl, or
    mono- or or di-(C1 to C4)alkylamino phenyl, in particular 2,6-di-(C1 to C4) alkylamino phenyl.

Preferably for above Amidinates and the Guanidinates Z1 and Z3 each comprise more carbon atoms than Z2, such as Z1 and Z3 each comprise 8 carbon atoms and more. Most preferably and independent of the above Z1 and Z3 are branched or substituted in one or more of the 2-positions.

The metal-complex comprises (exactly) one guanidinate- or (exactly) one amidinate-ligand per metal atom. Bimetal complexes may comprise one of above two guanidinate-ligands, two of above amidinate-ligands or one of above guanidinate- and one of above amidinate-ligand. Typically bimetal complexes become active as CCTP catalysts if used with a further coordinating ligand such as THF. Preferred are catalysts comprising only one metal per molecule.
2. The metal is Ti, Zr or Hf in the +2, +3 or +4 Formal Oxidation State, Preferably in the +4 Formal Oxidation State.

3. The Metal Complexes Preferably have the Following Structure

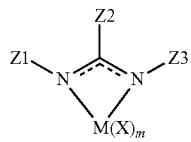
III wherein
M=Ti, Zr or Hf, preferably Ti or Zr,
X=independent of each m halogen, preferably Cl; hydrocarbyl, in particular C1 to C40, preferably C1 to C4, in particular methyl; hydride; alkoxide; amide, optionally substituted, NR1R2 with R1 and R2 as defined above, preferably NR1R2 is diethylamido, dimethylamido or methylethylamido; tetrahydrofuran; m=1 to 4,
with Z1, Z2 and Z3 as defined above.

Most preferably the metal complex has the following structure:

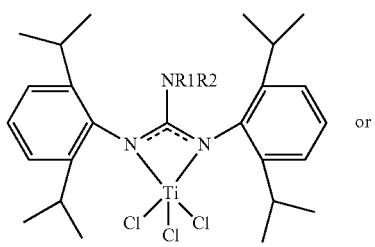
IV or

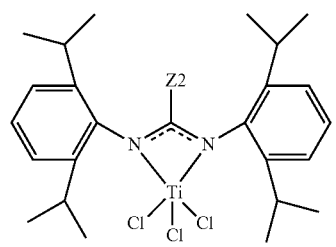
V with R1, R2 and Z2 as defined above.

The above mentioned complexes as defined by structures III, IV and V may also exist as anionic species with an additional cation $Q^+$ which is selected from the group of $R_4N^+$, $R_3NH^+$, $R_2NH_2^+$, $RNH_3^+$, $R_4P^+$ in which R is an alkyl, aryl, phenyl, hydrogen or halogen.

Examples of the above metal catalysts include
{N',N''-bis[2,6-di(1-methylethyl)phenyl]-N,N-dimethyl-guanidinato}metal(IV) chloride,
{N',N''-bis[2,6-di(1-methylethyl)phenyl]-N,N-diethyl-guanidinato}metal(IV) chloride,
{N',N''-bis[2,6-di(1-methylethyl)phenyl]-N,N-pentamethylene-guanidinato}metal (IV) chloride,
{N',N''-bis[2,6-di(1-methylethyl)phenyl]-N-cyclohexyl-N-methyl-guanidinato}metal (IV) chloride,
{N',N''-bis[2,6-di(1-methylethyl)phenyl]-N-cyclohexyl-N-methyl-guanidinato}metal (IV) chloride,
[Diethylammonium][N,N'-bis(2,6-diisopropylphenyl)-benzamidinato-tetrachloro]metalat(IV),
[Diethylammonium][N,N'-bis(2,6-diisopropylphenyl)-4-(dimethylamino)benzamidinato-tetrachloro]metalat(IV),
[Diethylammonium][N,N'-bis(2,6-diisopropylphenyl)-4-methoxybenzamidinato-tetrachloro]metalat(IV),
[Diethylammonium][N,N'-bis(2,6-diisopropylphenyl)-4-(2,5-dimethyl-1H-pyrrol-1-yl)benzamidinato-tetrachloro]metalat(IV),
[N,N'-bis(2,6-diisopropylphenyl)-4-(dimethylamino)benzamidinato-diethylamido]metal(IV) chloride,
[N,N'-bis(2,6-diisopropylphenyl)-4-(2,5-dimethyl-1H-pyrrol-1-yl)benzamidinato-diethylamido]metal(IV) chloride,
with metal=titan, zirconium or hafnium. Metal catalysts wherein Z1 and Z3 are different are also possible (3c,3d,4c,4d):

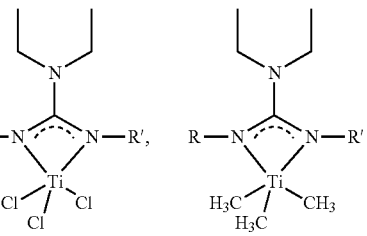

3a R = R' = 2,6-$^i$PrPh
3b R = R' = 2,6-MePh
3c R = 2,6-MePh, R' = 2,6-$^i$PrPh
3d R = 2,6-MePh, R' = $^t$Bu

4a R = R' = 2,6-$^i$PrPh
4b R = R' = 2,6-MePh
4c R = 2,6-MePh, R' = 2,6-$^i$PrPh
4d R = 2,6-MePh, R' = $^t$Bu

Alternatively, the metal complex maybe formed in situ from suitable transition metal and ligand precursors. The structure of the resulting in situ complex is as defined for the preformed complexes above.

The transition metal precursor may be any Ti, Zr or Hf complex capable of reacting with a ligand precursor to form a guanidinate or amidinate complex as described above in situ.

Examples of such transition metal precursor (with M=Ti, Zr or Hf) include:
  $MX_4$ where each X may independently halogen {F, Cl, Br, I}, hydride {H}, hydrocarbyl {R, e.g. benzyl}, alkoxide {OR} or amide {NR1R2});
  $MX_4L_2$ where each X may independently halogen {F, Cl, Br, I}, hydride {H}, hydrocarbyl {R, e.g. benzyl}, alkoxide {OR} or amide {NR1R2} with L equals any two electron donor ligand, e.g. ethers such as tetrahydrofuran, or di-ethylether, acetonitrile, or trihydrocarbylphosphine;
  $M(acac)_4$, where acac=2,4-pentanedionato, 1,1,1,5,5,5-hexafluoro-2,4-pentanedionato or 2,2,6,6-tetramethyl-3,5-heptanedionato;
  $M(O_2CR)_4$, where $O_2CR$ is any carboxylic acid anion, e.g. 2-ethylhexanoate.

The ligand precursor may be any compound capable of reacting with a transition metal precursor to form an amidine or guanidine complex in situ. Examples of such ligand precursor include:

Dihydrocarbylcarbodiimides, such as bis(2,6-diisopropylphenyl)carbodiimide or dicyclohexylcarbodiimide, Diheterohydrocarbylcarbodiimides, such as bis(2-methoxyphenyl)-carbodiimide;

Amidate or guanidate salts, e.g. lithium 1,3-dihydrocarbylamidate or lithium 1,3-dihydrocarbylguanidate.

Amidines or guanidines, such as N,N'-bis(2,6-diisopropylphenyl)benzimidamide or 2,3-bis(2,6-diisopropylphenyl)-1,1-dihydrocarbylguanidine 4. The Metal Complexes become a Catalyst for CCTP when Combined at Least with a Co-catalyst.

The co-catalyst, without being bound to the theory, acts as a chain transfer agent and may optionally act in addition as an activator for the complex in order that the complex becomes the (active) catalyst.

The co-catalyst and chain transfer agent is an organo aluminium, preferably an alkyl aluminium, or an organo zinc, preferably an alkyl zinc, or mixtures thereof.

Most preferably the co-catalyst is selected from:
tri hydrocarbyl aluminium, wherein the hydrocarbyl is for example methyl, ethyl, propyl, isopropyl, n-butyl, isobutyl, pentyl, neopentyl or isopentyl or a mixtures thereof, preferably tri(methyl and/or ethyl) aluminium,
di-hydrocarbyl zinc, wherein the hydrocarbyl is for example methyl, ethyl, propyl, isopropyl, n-butyl, isobutyl, pentyl, neopentyl or isopentyl or a mixtures thereof, preferably di(methyl and/or ethyl) zinc,
a mixture of tri hydrocarbyl aluminium and di-hydrocarbyl zinc reagents as described above,
oligomeric or polymeric hydrocarbyl alumoxanes, preferably oligomeric or polymeric methyl alumoxanes (including modified methylalumoxane modified by reaction of methylalumoxane with triisobutyl aluminium or isobutylalumoxane),
hydrocarbyl aluminium halogenides such as dialkyl aluminium halogenides, alkyl aluminium dihalogenides, with alkyl preferably being C1 to C3-alkly,
hydrocarbyl aluminium sesqui halogenides, preferably, methyl aluminium sesqui halogenides,
or mixture thereof.

The most preferred co-catalyst for use in forming the (active) catalysts is triethylaluminium or a mixture of triethylaluminium comprising minor portions of diethylaluminiumhydrid (such as below 10 wt. %).

5. In Addition to the Co-catalyst for Certain Embodiments an Activator may be Present The activator may comprise a boron containing compound. More preferably the activator comprises pentafluorophenyl boranes and pentafluorophenyl borates. Illustrative examples of boron compounds which may be used as activator in the preparation of catalysts of this invention are tri-substituted (alkyl) ammonium salts such as trimethylammonium tetraphenylborate, triethylammonium tetraphenylborate, tripropylammonium tetraphenylborate, tri(n-butyl) ammonium tetraphenylborate, tri(t-butyl)ammonium tetraphenylborate, N,N-dimethylanilinium tetraphenylborate, N,N-diethylanilinium tetraphenylborate, N,N-dimethyl-2,4,6-trimethylanilinium tetraphenylborate, trimethylammonium tetrakis(pentafluorophenyl)borate, triethylammonium tetrakis(pentafluorophenyl)borate, tripropylammonium tetrakis(pentafluorophenyl)borate, tri (n-butyl)ammonium tetrakis(pentafluorophenyl)borate, tri (sec-butyl)ammonium tetrakis(pentafluorophenyl)borate, dioctadecylmethylammonium tetrakis(pentafluorophenyl) borate, dioctadecylmethylammonium tetrakis-(3,5-bis(trifluoromethyl)-phenyl)borate, N,N-dimethylanilinium tetrakis(pentafluorophenyl)borate, N,N-dimethylanilinium n-butyltris(pentafluorophenyl)borate, N,N-dimethylanilinium benzyltris(pentafluorophenyl)borate, N,N-dimethylanilinium tetrakis(4-(t-butyldimethylsilyl)-2,3,5,6-tetrafluorophenyl)borate, N,N-dimethylanilinium tetrakis(4-(triisopropylsilyl)-2,3,5,6-tetrafluorophenyl)borate, N,N-dimethylanilinium pentafluorophenoxytris (pentafluorophenyl)borate, N,N-diethylanilinium tetrakis (pentafluorophenyl)borate, N,N-dimethyl-2,4,6-trimethylanilinium tetrakis(pentafluorophenyl)borate, trimethylammonium tetrakis(2,3,4,6-tetrafluorophenyl)borate, triethylammonium tetrakis(2,3,4,6-tetrafluorophenyl) borate, tripropylammonium tetrakis(2,3,4,6-tetrafluorophenyl)borate, tri(n-butyl)-ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate, and N,N-dimethyl-2,4,6-trimethylanilinium tetrakis(2,3,4,6-tetrafluorophenyl)borate;

dialkyl ammonium salts such as: di-(i-propyl)ammonium tetrakis(pentafluorophenyl)borate, and dicyclohexylammonium tetrakis(pentafluorophenyl)borate; tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate;

di-substituted oxonium salts such as: diphenyloxonium tetrakis(pentafluorophenyl)borate, di(o-tolyl)oxonium tetrakis(pentafluorophenyl)borate, and di(2,6-dimethyl-phenyl)oxonium tetrakis(pentafluorophenyl)borate;

di-substituted sulfonium salts such as: diphenylsulfonium tetrakis(pentafluorophenyl)borate, di(o-tolyl)sulfonium tetrakis(pentafluorophenyl)borate, and bis(2,6-dimethylphenyl)sulfonium tetrakis(pentafluorophenyl)borate.

Preferred cations are ammonium borates such as trialkylammonium tetrakis-(pentafluorophenyl)borates and in particular $[R_2N(CH_3)H]^+[B(C_6F_5)_4]^-$ with $R=C_{16}H_{33}-C_{18}H_{37}$.

Preferably if trialkyl aluminium compounds are used as (sole) co-catalyst an activator as described above is applied.

6. Preparation of the Metal Complex

One mode of preparing the complexes is characterized in that a substituted carbodiimid is reacted with a derivative of a transition metal selected from Ti, Zr or Hf (see scheme 1).

The transition metal derivative can be selected from transition metal amido halides. The preferred transition metal derivative is (chloro)(amido)metal(IV), with metal=titanium, zirconium or hafnium.

The amido transition metal complex is available through reaction of the transition metal halide having the oxidation state 4 with 2 equivalents of amine or by reaction with one equivalent of lithium amide.

Scheme 1

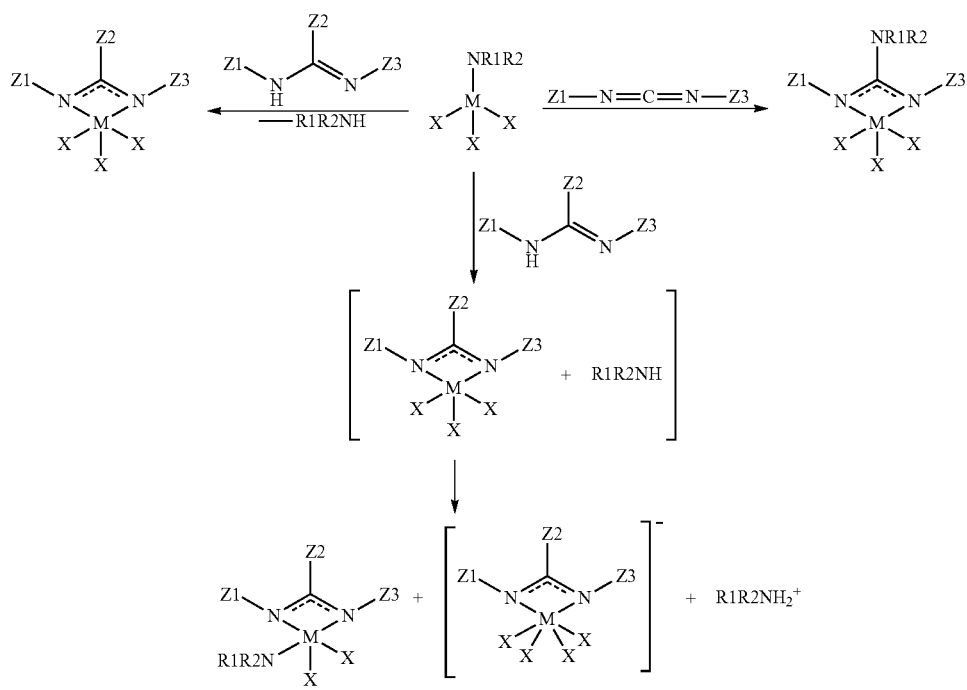

The catalyst having a guanidinate ligand is available by reacting di-substituted carbodiimide with the derivative of the transition metal amido complex, in a solvent, preferably toluene to result in the corresponding guanidinato transition metal complex. In this case the transition metal derivative as starting compound is (chloro)(amido)metal(IV) with amido=NR1R2, metal and R1 and R2 as defined above.

Moreover, the catalyst, especially the amidinato based complexes can be derived by reaction of the corresponding transition metal halide with the pre-synthesised ligand. The ligand can be synthesised by reacting the substituted or non-substituted carbodiimid with a lithiated aromatic compound.

Suitable reaction media or the formation of the catalysts complex and or ligand include aliphatic and aromatic hydrocarbons, ethers, and cyclic ethers, particularly C4 to C20 hydrocarbons, linear and/or branched, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, tetrahydrofuran, dioxane, propylencarbonate, dimethylformamide or n-methyl-2-pyrrolidone. Mixtures of the foregoing are also suitable.

7. The (Activated) Catalyst

The catalysts are rendered catalytically active by combination with an activating co-catalyst to form the catalyst complex or by combination with a co-catalyst and an activator.

In addition to above mentioned co-catalysts an activator can be used or is to be used when the co-catalyst on its own is not activating. If the respective co-catalyst is selected from the alkyl aluminium compounds use of activator is preferable. Suitable activators are referenced above.

The foregoing co-catalysts and activating techniques have been previously taught with respect to different metal complexes in the following references: EP 277003, U.S. Pat. Nos. 5,153,157, 5,064,802, EP 468651 and EP 520732 the teachings of which are hereby incorporated by reference.

The molar ratio of catalyst to co-catalyst with reference to the [Ti, Zr and/or Hf] to [Al and/or Zn] atomic ratio preferably is from 1:50 to 1:1000000, more preferably 1:2000 to 1:100000 and most preferably 1:10000 to 1:40000.

A support, especially silica, alumina, magnesium chloride, or a polymer (especially poly(tetrafluoroethylene) or a polyolefin) may also be applied. The support is preferably used in an amount to provide a weight ratio of catalyst (based on metal): support from 1:100000 to 1:10, more preferably from 1:50000 to 1:20, and most preferably from 1:10000 to 1:30.

8. Process

According to the process of the invention ethylene or ethylene and propylene or propylene are converted to oligomeric or polymeric hydrocarbon moieties in the presence of above metal complex and above co-catalysts optionally including above activators.

The oligomeric or polymeric hydrocarbon moieties obtained are terminated by the co-catalyst moiety, e.g. an aluminium or zinc moiety. The aluminium or zinc moiety originates from the above co-catalysts or a derivative thereof.

In general, the polymerization may be accomplished at temperatures from 0 to 100° C., preferably 30 to 80° C., and pressures from 1 to 100 bar, preferably 1 to 30 bar. In general, shorter carbon chains can be produced if the reaction temperature is increased. Suspension, solution, slurry, gas phase, solid state powder polymerization or other process condition may be applied if desired.

Suitable solvents for polymerization are inert liquids. Suitable solvents include aliphatic and aromatic hydrocarbons, ethers, and cyclic ethers, particularly C4 to C20 hydrocarbons, linear and/or branched, and mixtures thereof (including monomers subject to polymerization, especially the previously mentioned addition polymerizable monomers); cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

Desirably the polymerization is conducted by contacting the monomer(s) and catalyst composition under conditions to produce an oligomer or a polymer having molecular weight (MW) from 100 to 1000000, preferably 100 to 10000, most preferably 300 to 1000.

In particular it may be wanted that very low molecular oligomers (100 to 400 g/mol) or low molecular oligomers (300 to 1000 g/mol) are produced. For determination of the molecular weight distribution gel permeation chromatography (GPC) or mass spectroscopy may be used.

GPC-samples were prepared by dissolving the polymer (0.05 wt.-%, conc.=1 mg/mL) in the mobile phase solvent in an external oven and were run without filtration. The molecular weight was referenced to polyethylene (Mw=520 to 3200000 gmol$^{-1}$) and polystyrene (Mw=580 to 2800000 gmol$^{-1}$).

Molecular weight distribution (Mw/Mn) was determined by gel permeation chromatography on a Polymer Laboratories Ltd. PL-GPC220 chromatograph at 150° C. using 1,2, 4-trichlorobenzene as the mobile phase and Mw/Mn is typically between 1 and 6 or 1.7 and 2.5.

It has been observed that the molecular weight of the aluminium or zinc terminated oligomeric or polymeric hydrocarbons can be influenced as follows:
  a) high temperatures result in lower molecular weights, in particular for titanium catalysts,
  b) a higher Al/Zn to complex ratio generally results in lower molecular weights,
  c) a shorter reaction time may result in lower molecular weights, in particular for complexes comprising Zr,
  d) high monomer concentrations result in higher molecular weights,
  e) polymerization runs carried out with triethyl aluminium—in comparison with other organo aluminium co-catalysts—resulted in lower molecular weight products.

Zr-complexes are compared to Ti-complexes more sensitive to above measures and, therefore, can produce lower molecular weights.

9. Conversion of the Aluminium or Zinc Terminated Oligomeric or Polymeric Hydrocarbons The aluminium or zinc terminated oligomers or polymers are preferably oxidized by using a gas comprising oxygen, such as air or oxygen. The oxidized oligomers or polymers can be further hydrolyzed to yield OH-substituted products having the OH group at the terminal position.

The oxidation can be done in the same reaction medium as defined above for the polymerization or in a different solvent. The oxidation is done by reacting the aluminium terminated oligomers or polymers with air or oxygen or mixtures of oxygen and other gases, selected from noble gases or $N_2$. Suitable reaction temperatures range from 10 to 100° C., preferably 30 to 60° C.

Additionally an oxidation catalyst may be used in order to promote the reaction or to prevent side products as known in the art. The oxidation catalyst is preferably the metal catalyst used in the CCTP or its decomposition product.

Subsequently the oxidized product can be hydrolyzed via addition of water or alcohols at temperatures ranging from 10 to 100° C., preferably 30 to 60° C. The hydrolysis may be carried out in the presence of sulphuric acid or ammonia. The oxidation reaction and the benefit resulting from the presence of Ti-compounds during oxidation is described in more detail in GB 1309469 and U.S. Pat. No. 3,641,085, whereas U.S. Pat. No. 3,419,352 relates to the presence of $NH_3$ during the hydrolysis.

Alternatively the aluminium or zinc terminated oligomers or polymers may be transformed into olefins by techniques known to the skilled artisan. Such processes include β-hydrid elimination, e.g. induced through thermal treatment, or substitution with ethylene or propylene.

The products obtained are long chain based on ethylene or ethylene and propylene alcohols with a terminal hydroxy group. The products are oligomers or polymers and may also be called functionalised waxes, if solid at room temperature and melting below 120° C.

The long chain alcohols can be further functionalized to obtain derivatives as described in EP 0329891 A2 or in Dirk Schär and Clemens Schröder: "Long Chain Linear Fatty Alcohols from ZIEGLER-Synthesis, their Mixtures, Derivatives and Use", Sasol Germany GmbH: IP.com Prior Art Database Disclosure, Disclosure Number IPCOM000203049D dated 17 Jan. 2011.

The wax products may be used as described by Madelein vd Merwe (Kleyn), Thorsten Butz, Thomas Haas, Michael Matthäi, Gernot Meyer and Norbert Pete-reit in "Fischer-Tropsch Waxes—Production, Properties and Applications", Sasol Wax GmbH, IP.com Prior Art Database Disclosure, Disclosure Number IPCOM000126507D dated 22 Jul. 2005.

EXAMPLES

The handling of air- or moisture-sensitive compounds was carried out under $N_2$ using glove-box, standard Schlenk, or vacuum-line techniques. Solvents and reagents were purified by distillation from $LiAlH_4$, potassium, Na/K alloy, or sodium ketyl of benzophenone under nitrogen immediately before use.

Toluene (Aldrich, anhydrous, 99.8%) was passed over columns of $Al_2O_3$ (Fisher Scientific), BASF R3-11 supported Cu oxygen scavenger, and molecular sieves (Aldrich, 4 Å). Ethylene (AGA polymer grade) was passed over BASF R3-11 supported Cu oxygen scavenger and molecular sieves (Aldrich, 4 Å). NMR spectra were recorded on a Varian Inova 400 ($^1$H: 400 MHz, $^{13}$C: 100.5 MHz) or Varian Inova 300 (1H: 300 MHz, 13C: 75.4 MHz) spectrometer. The $^1$H and $^{13}$C NMR spectra, measured at 26° C. and 120° C., were referenced internally using the residual solvent resonances and the chemical shifts are reported in ppm. The polymer samples were prepared by dissolving 15 mg of the polymer in 0.5 mL $C_2D_2Cl_4$ at 100° C. for 3 h before measuring. Gel permeation chromatography (GPC) analysis was carried out on a PL-GPC 220 (Agilent, Polymer Laboratories) high temperature chromatographic unit equipped with LS, DP and RI detectors and two linear mixed bed columns (Olexis, 13-micron particle size) at 150° C. using 1,2,4-trichlorobenzene as the mobile phase. The samples were prepared by dissolving the polymer (0.05 wt.-%) in the mobile phase solvent in an external oven and were run without filtration. The molecular weight was referenced to polyethylene (Mw=520–3200000 gmol$^{-1}$) and polystyrene (Mw=580–2800000 gmol$^{-1}$) standards. The reported values are the average of at least two independent determinations.

N,N-dimethylanilinium (tetrapentafluorophenyl) borate ([PhNMe$_2$H][B(C$_6$F$_5$)$_4$], abcr GmbH & Co. KG), N,N,N-trialkylammonium (tetrapenta fluorophenyl) borate ([R$_2$NMeH][B(C$_6$F$_5$)$_4$], R=C$_{16}$H$_{33}$—C$_{18}$H$_{37}$, 6.2 wt % B(C$_6$F$_5$)$_4$ in Isopar, DOW Chemicals), trimethyl aluminium (TMA, 2.0 M in toluene, Aldrich), triethyl aluminium (TEA, 25 wt % in toluene, Aldrich), tri-iso-butyl aluminium (TIBA, 25 wt % in toluene, Aldrich), tri-n-octylaluminium (TOA, 25 wt % in toluene, Aldrich), EURECEN Al 5100-10-toluene (4.9 wt % in Al, Chemtura Organometallics), titanium(IV) isopropoxide (Acros Organics), and bis(2,6-diisopropylphenyl)carbodiimide (TCI Europe) were used as received. dry-MAO was prepared by removal of volatiles from EURECEN Al 5100. Titanium precursors (Et$_2$NTiCl$_3$; C$_5$H$_{10}$NTiCl$_3$; Me(Cy)NTiCl$_3$) were synthesized by a method reported in E. Benzing, W. Kornicker, *Chem. Ber.* 1961, 94, 2263-2267.

The chain transfer agents used are the aluminium compounds described above. After the desired reaction time the ethylene flow was terminated and the reactor was vented and slowly pressurized with dry oxygen to reach 2 bar total pressure. After 15 min oxidation 1 mL of a titanium(IV) isopropoxide solution in toluene (1 M) was injected and the autoclave was heated to reach 90° C. inside. After four hours the residual aluminium alkyls were destroyed by addition of 50 mL of ethanol. Polymeric product was collected, stirred for 30 min in acidified ethanol and rinsed with ethanol and acetone on a glass frit. The polymer was initially dried on air and subsequently in vacuum at 80° C.

The following abbreviations were used:
Me—Methyl (CH$_3$)
Et—Ethyl (CH$_3$CH$_2$)
i-Pr—iso-Propyl (Me$_2$CH)
i-Bu—iso-Butyl (Me$_2$CHCH$_2$)
Cy—Cyclohexyl (C$_6$H$_{11}$)
Oct—Octyl (C$_8$H$_{17}$)
MAO—Methylaluminiumoxane [(MeAlO)$_n$.(Me$_3$Al)$_{1/3 n}$]
d-MAO—dry-Methylaluminoxane [(MeAlO)$_n$]
TMA—Trimethylaluminium (Me$_3$Al)
TEA—Triethylaluminium (Et$_3$Al)
TIBA—Tri-iso-butyl aluminium (i-Bu$_3$Al)
TOA—Trioctylaluminium (Oct$_3$Al)
Pi—Piperidin-1-yl(C$_5$H$_{10}$N)

Example 1

Synthesis of {N',N''-bis[2,6-di(1-methylethyl)phenyl]-N,N-diethyl-guanidinato}titan(IV) chloride {[Et$_2$NC(2,6-Pr$^i_2$C$_6$H$_3$N)$_2$]TiCl$_3$; complex A}

Diethylamidotitanium(IV) chloride (0.50 g, 2.2 mmol) and Bis(2,6-diisopropylphenyl) carbodiimide (0.80 g, 2.2 mmol) were subsequently added to a Schlenk flask filled with 25 mL of toluene and stirred at 50° C. After 24 h the mixture was heated to 110° C. and filtered. Slow cooling to room temperature gives dark red crystals. The supernatant solution was decanted and the titanium complex was dried under reduced pressure (1.05 g, 80% yield).

$^1$H-NMR (C$_6$D$_6$, 400 MHz, 298K): δ=0.36 (t, 6H, CH$_2$CH$_3$), 1.15 (d, 12H, CH(CH$_3$)$_2$), 1.52 (d, 12H, CH(CH$_3$)$_2$), 2.52 (q, 4H, CH$_2$CH$_3$), 3.57 (m, 4H, CH(CH$_3$)$_2$), 7.0-7.11 (m, 6H, C$_6$H$_3$) ppm.

Example 2

Synthesis of {N',N''-bis[2,6-di(1-methylethyl)phenyl]-N-methyl-N-cyclohexyl-guanidinato}titan(IV) chloride {[Me(Cy)NC(2,6-Pr$^i_2$C$_6$H$_3$N)$_2$]TiCl$_3$; complex B}

Cyclohexyl(N-methyl)amidotitanium(IV) chloride (0.78 g, 2.93 mmol) and Bis(2,6-diisopropylphenyl) carbodiimide (1.06 g, 2.9 mmol) were subsequently added to a Schlenk flask filled with 25 mL of toluene and stirred at 50° C. After 24 h the mixture was heated to 110° C. and filtered. Slow cooling to room temperature gives dark red crystals. The supernatant solution was decanted and the titanium complex was dried under reduced pressure (0.92 g, 50% yield).

$^1$H-NMR (C$_6$D$_6$, 400 MHz, 298K): δ=0.46 (m, 2H, CH$_2$), 0.71 (m, 4H, CH$_2$), 1.08 (m, 4H, CH$_2$), 1.17 (d, 6H, CH(CH$_3$)$_2$), 1.22 (d, 6H, CH(CH$_3$)$_2$), 1.55 (d, 12H, CH(CH$_3$)$_2$), 1.90 (s, 3H, CH$_3$), 3.33 (m, 1H, CH(CH$_2$)$_2$), 3.49 (m, 2H, CH(CH$_3$)$_2$), 3.75 (m, 2H, CH(CH$_3$)$_2$), 7.04-7.14 (m, 6H, C$_6$H$_3$) ppm.

Example 3

Synthesis of {N',N''-bis[2,6-di(1-methylethyl)phenyl]-N,N-pentamethylene-guanidinato}titanium(IV) chloride {[PiC(2,6-Pr$^i_2$C$_6$H$_3$N)$_2$]TiCl$_3$; complex C}

Piperidin-1-yltitanium(IV) chloride (0.80 g, 3.36 mmol) and Bis(2,6-diisopropylphenyl) carbodiimide (1.22 g, 3.36 mmol) were subsequently added to a Schlenk flask filled with 25 mL of toluene and stirred at 50° C. After 24 h the mixture was heated to 110° C. and filtered. Slow cooling to room temperature gives dark red crystals. The supernatant solution was decanted and the titanium complex was dried under reduced pressure (1.80 g, 89% yield).

$^1$H-NMR (C$_6$D$_6$, 400 MHz, 298K): δ=0.71 (m, br, 6H, (CH$_2$)$_3$), 1.17 (d, 12H, CH(CH$_3$)$_2$), 1.53 (d, 12H, CH(CH$_3$)$_2$), 2.56 (m, br, 4H, NCH$_2$), 3.63 (m, 4H, CH(CH$_3$)$_2$), 7.05-7.14 (m, 6H, C$_6$H$_3$) ppm.

Example 4

Synthesis of {N',N'''-bis[2,6-di(methyl)phenyl]-sec-butyl-aminidinato}titanium(IV) chloride [{secBuC(N-2,6-Me$_2$C$_6$H$_3$)$_2$}TiCl$_4$][Et$_2$NH$_2$]; complex D

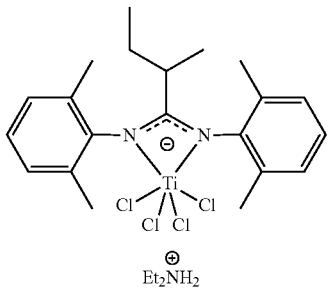

N,N'-bis(2,6-dimethylphenyl)-2-methylbutanimidamide (0.311 g, 1.01 mmol) and (diethylamino)titanium(IV) chloride (0.228 g, 1.01 mmol) were dissolved in dried toluene (40 mL) and stirred over night at ambient temperature. The red solution was filtered out leaving behind yellow solid. The filtrate was layered with hexane to give dark red crystals (no yield determined)

1H-NMR (300 MHz, C6D6): δ=0.40 (tr. J=7.3 Hz, 3H, CHCH$_2$CH$_3$), 0.78 (d, J=7.2 Hz, 3 H, CHCH$_3$), 0.97 (pent, J=6.6 Hz, 2 H, CCH$_2$), 1.08 (tr. J=7.2 Hz, 6 H, N(CH$_2$CH$_3$)$_2$, 2.43 (q. J=6.5 Hz, 4 H, N(CH$_2$CH$_3$)$_2$), 2.92 (s. 6 H, Ar—CH$_3$), 2.96 (s. 6 H, Ar—CH$_3$), 6.92-7.12 (m, 6 H, Ar—H), 8.85 (s, 2 H, NH$_2$) ppm.

Example 5

Ethylene Polymerization (Runs 1-15)

The catalytic ethylene polymerization reactions were performed in a 250 mL glass autoclave (Büchi) in semi-batch mode (ethylene was added by a replenishing flow to keep the pressure constant). The reactor was ethylene flow controlled and equipped with separated toluene, catalyst and co-catalyst injection systems.

During a polymerization run the pressure and the reactor temperature were kept constant while the ethylene flow was monitored continuously. In a typical semi-batch experiment, the autoclave was evacuated and heated for 1 h at 80° C. prior to use. The reactor was then brought to desired temperature, stirred at 1000 rpm and charged with 150 mL of toluene.

After pressurizing with ethylene to reach 2 bar total pressure the autoclave was equilibrated for 10 min. Successive co-catalyst solution, activator, and 1 mL of a 0.002 M pre-catalyst stock solution in toluene was injected, to start the reaction. After 15 min reaction time the reactor was vented and the residual aluminium alkyls were destroyed by addition of 50 mL of ethanol. Polymeric product was collected, stirred for 30 min in acidified ethanol and rinsed with ethanol and acetone on a glass frit. The polymer was initially dried on air and subsequently in vacuum at 80° C.

TABLE 1

Ethylene polymerization with MAO and d-MAO co-catalysts

| Entry | Complex | Cocat. | T [° C.] | $m_{Pol.}$ [g] | Activity [kg$_{PE}$mol$_{cat}^{-1}$h$^{-1}$bar$^{-1}$] | $M_n$ [kgmol$^{-1}$] | $M_w/M_n$ |
|---|---|---|---|---|---|---|---|
| 1 | A | MAO | 30 | 2.82 | 2820 | 15.9 | 2.0 |
| 2 | A | MAO | 50 | 1.67 | 1670 | 8.4 | 2.5 |
| 3 | A | MAO | 80 | 0.10 | 100 | 7.6 | 4.0 |
| 4 | B | MAO | 30 | 1.91 | 1910 | 13.2 | 4.8 |
| 5 | B | MAO | 50 | 4.20 | 4200 | 6.5 | 2.5 |
| 6 | B | MAO | 80 | 0.95 | 950 | 3.3 | 2.0 |
| 7 | C | MAO | 50 | 4.50 | 4500 | 6.2 | 3.0 |
| 8 | A | d-MAO | 30 | 3.64 | 3640 | 829.2 | 5.9 |
| 9 | A | d-MAO | 50 | 1.36 | 1360 | 172.5 | 3.3 |
| 10 | A | d-MAO | 80 | 1.22 | 1220 | 75.6 | 2.7 |
| 11 | B | d-MAO | 30 | 9.30 | 9300 | 104.1 | 4.0 |
| 12 | B | d-MAO | 50 | 1.92 | 1920 | 85.3 | 2.8 |
| 13 | B | d-MAO | 80 | 1.08 | 1080 | 34.7 | 2.5 |
| 14 | C | d-MAO | 50 | 3.35 | 3350 | 111.6 | 5.7 |
| 15 | D | d-MAO* | 50 | 0.89 | 894 | 1406 | 5.1 |

Complex: 2.0 μmol; co-catalyst: 1.0 mmol (Ti/Al = 1/500); toluene: 150 mL; p = 2 bar; t = 15 min;
*250 equiv. d-MAO.

In table 1 it is shown that the ethylene polymerization is influenced by the aluminium alkyl activator used and the reaction temperature.

The stability of the titanium complexes in combination with fully suppressed β-H elimination allows for the synthesis of linear saturated long-chain polymers. With increasing temperature shorter chain length were produced, while in TMA free d-MAO higher activities and higher molecular weights are observed.

Table 2 shows the dependence of the results of the ethylene polymerization on the nature of the aluminium alkyl used and the catalyst to aluminium ratio for complex A to C. In general with higher Al to Ti ratios shorter polymer chain were observed, while the shortest chains were produced by the use of TEA.

For TEA co-catalyst/transfer reagent relative short chain lengths could be observed by SEC while for the stronger coordinating TMA and the sterically hindered TIBA the chain transfer was delayed resulting in increasing molecular weights.

TABLE 2

Ethylene polymerization with trialkylaluminium co-catalysts and perfluorophenylborate activator

| Entry | Complex | Cocat. | Al/Ti | T [° C.] | $m_{Pol.}$ [g] | Activity [$kg_{PE}mol_{cat}^{-1}h^{-1}bar^{-1}$] | $M_n$ [kgmol$^{-1}$] | $M_w/M_n$ |
|---|---|---|---|---|---|---|---|---|
| 16 | A | TEA | 250 | 50 | 1.50 | 1500 | 2.9 | 2.3 |
| 17 | A | TEA | 500 | 50 | 1.62 | 1620 | 2.2 | 1.9 |
| 18 | A | TEA | 750 | 50 | 1.53 | 1530 | 2.1 | 2.4 |
| 19 | A | TEA | 1000 | 50 | 1.80 | 1800 | 1.8 | 1.9 |
| 20 | A | TMA | 500 | 50 | 0.70 | 700 | 3.9 | 1.9 |
| 21 | B | TEA | 250 | 50 | 0.92 | 920 | 3.9 | 2.5 |
| 22 | B | TEA | 500 | 50 | 1.70 | 1700 | 2.8 | 2.2 |
| 23 | B | TEA | 750 | 50 | 1.75 | 1750 | 2.1 | 2.0 |
| 24 | B | TEA | 1000 | 50 | 1.80 | 1800 | 1.6 | 2.0 |
| 25 | C | TEA | 250 | 50 | 1.50 | 1500 | 3.3 | 2.6 |
| 26 | C | TEA | 500 | 50 | 1.40 | 1400 | 3.1 | 2.4 |
| 27 | C | TEA | 750 | 50 | 1.40 | 1400 | 2.7 | 2.4 |
| 28 | C | TEA | 1000 | 50 | 1.55 | 1550 | 2.5 | 2.3 |

Complex: 2.0 μmol; ammonium borate: 2.2 μmol $[R_2N(CH_3)H]^+[B(C_6F_5)_4]^-$ (R = $C_{16}H_{33}$ – $C_{18}H_{37}$), Ti/B = 1/1.1; toluene: 150 mL; T = 50° C., p = 2 bar; t = 15 min.

The NMR investigation of the low molecular weight polymeric material revealed that all polymer chains are fully saturated and no olefinic proton resonances could be observed.

Example 6

Ethylene Polymerization (Runs 16-28)

The catalytic ethylene polymerization reactions were performed in a 250 mL glass autoclave (Büchi) in semi-batch mode (ethylene was added by a replenishing flow to keep the pressure constant). The reactor was ethylene flow controlled and equipped with separated toluene, catalyst and co-catalyst injection systems. During a polymerization run the pressure and the reactor temperature were kept constant while the ethylene flow was monitored continuously. In a typical semi-batch experiment, the autoclave was evacuated and heated for 1 h at 80° C. prior to use. The reactor was then brought to desired temperature, stirred at 1000 rpm and charged with 150 mL of toluene. After pressurizing with ethylene to reach 2 bar total pressure the autoclave was equilibrated for 10 min. Successive co-catalyst solution (TEA, TMA), activator (perfluorophenylborate) and 1 mL of a 0.002 M pre-catalyst stock solution in toluene was injected, to start the reaction. After 15 min reaction time the reactor was vented and the residual aluminium alkyls were destroyed by addition of 50 mL of ethanol. Polymeric product was collected, stirred for 30 min in acidified ethanol and rinsed with ethanol and acetone on a glass frit. The polymer was initially dried on air and subsequently in vacuum at 80° C.

Example 7

Ethylene Polymerization Experiments (Runs 29-37)

The catalytic ethylene polymerization reactions were performed in a stainless steel 800 mL autoclave (Büchi) in semi-batch mode (ethylene was added by a replenishing flow to keep the pressure constant). The reactor was pressure, temperature, stirrer speed, and ethylene flow controlled and equipped with separated toluene, catalyst and co-catalyst injection systems. During a polymerization run the pressure and the reactor temperature were kept constant while the ethylene flow, inner and outer temperature, and stirrer speed were monitored continuously. In a typical semi-batch experiment, the autoclave was evacuated and heated for 1 h at 130° C. prior to use.

The reactor was then brought to desired temperature, stirred at 600 rpm and charged with 250 mL of toluene. After pressurizing with ethylene to reach the desired total pressure the autoclave was equilibrated for 10 min. Successive co-catalyst solution, activator, and pre-catalyst stock solution in toluene (0.002 M) was injected to start the reaction. After 60 min reaction time the reactor was vented and slowly pressurized with dry oxygen to reach 2 bar total pressure. After 15 min 1 mL of a titanium(IV)isopropoxide solution in toluene (1 M) was injected and the autoclave was heated to reach 90° C. inside. After four hours the residual aluminium alkyls were destroyed by addition of 50 mL of ethanol. Polymeric product was collected, stirred for 30 min in acidified ethanol and rinsed with ethanol and acetone on a glass frit. The polymer was initially dried on air and subsequently in vacuum at 80° C.

TABLE 3

Ethylene polymerization with trialkylaluminium co-catalysts
and perfluorophenylborate activators and subsequent oxidation

| Entry | Complex [μmol] | Cocat. | Al/Ti | T [° C.] | $m_{Pol.}$ [g] | Activity [$kg_{PE}mol_{cat}^{-1}h^{-1}bar^{-1}$] | $M_n$ [kgmol$^{-1}$] | $M_w/M_n$ |
|---|---|---|---|---|---|---|---|---|
| 29 | A   | 4   | TEA | 2500  | 70 | 44.0 | 5500  | 1.7 | 1.8 |
| 30 | A[b] | 2   | TEA | 5000  | 70 | 47.0 | 4700  | 2.1 | 1.9 |
| 31 | A[b] | 0.6 | TEA | 17000 | 65 | 28.4 | 9470  | 2.5 | 1.8 |
| 32 | A[b] | 0.4 | TEA | 25000 | 60 | 32.0 | 16000 | 3.3 | 1.9 |
| 33 | A[b] | 0.3 | TEA | 33000 | 65 | 24.4 | 16300 | 2.5 | 1.9 |
| 34 | A[b] | 0.2 | TEA | 50000 | 60 | 16.7 | 16700 | 2.9 | 1.9 |
| 35 | C   | 4   | TEA | 2500  | 60 | 30.2 | 3780  | 1.7 | 2.0 |
| 36 | C   | 4   | TEA | 2500  | 65 | 27.7 | 3460  | 1.5 | 2.0 |
| 37 | C   | 4   | TEA | 2500  | 75 | 4.20 | 525   | 0.9 | 1.6 |

Ammonium borate: $[R_2N(CH_3)H]^+[B(C_6F_5)_4]^-$ (R = $C_{16}H_{33}$ – $C_{18}H_{37}$), Ti/B = 1/1.1; toluene: 250 mL; p = 2 bar; t = 60 min;
[b] p = 5 bar.

Table 3 presents the results of the ethylene polymerization in presence of the catalyst resulting from complex A-C and subsequent oxidation of the Al terminated waxes.

As the results show the titanium catalyst can withstand remarkable high Al to Ti ratios up to 50000 equivalents at increased activity. The oxidation step yields hydroxyl terminated PE-oligomers. With higher Al to Ti ratios a shorter chain length of the alcohols was observed. NMR investigation of the low molecular weight polymeric material after oxidation and subsequent acidic work up revealed that approximately 80% of the Al-terminated polymer was oxidized resulting in long chain alcohol (detected by the presence of the HO—CH$_2$-methylene proton resonances at 3.58 ppm). The remaining 20% consist of non oxidized fully saturated waxes.

Example 8

Synthesis of {N',N''-bis[2,6-di(1-methylethyl)phenyl]-N,N-diethyl-guanidinato}-(diethylamido)zirconium(VI) chloride {[Et$_2$NC(2,6-Pr$^i_2$C$_6$H$_3$N)$_2$](Et$_2$N)ZrCl$_2$(THF); complex D; mixtures of isomers}

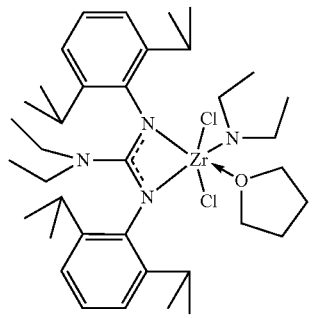

Zirconium precursors (Et$_2$N)$_4$Zr (D. C. Breadley, I. M. Thomas, J. Chem. SOC. 1960, 3857) and (Et$_2$N)$_2$ZrCl$_2$(THF)$_2$ (S. Brenner, R. Kempe, P. Arndt, Z. anorg. allg. Chem. 1995, 621, 2021-2024) were synthesized according to published procedures. (Z)-2,3-bis(2,6-diisopropylphenyl)-1,1-diethylguanidine was synthesized analogue to a procedure described in G. Jin, C. Jones, P. C. Junk, K.-A. Lippert, R. P. Rose, A. Stasch, New J. Chem., 2009, 33, 64-75.

Method A: Dichloro-bis(diethylamido)zirconium(IV)-bis (tetrahydrofurane) (0.036 g, 80 μmol) and Bis(2,6-diisopropylphenyl) carbodiimide (0.029 g, 80 μmol) were subsequently added to a Schlenk flask filled with 10 mL of toluene and stirred at RT. After 24 h the mixture was filtered and deluted with toluene to reach 40 mL. This solution when used results in the same oligomerization results as method B described below.

Method B: Dichloro-bis(diethylamido)zirconium(IV)-bis (tetrahydrofurane) (0.036 g, 80 μmol) and (Z)-2,3-bis(2,6-diisopropylphenyl)-1,1-diethylguanidine (0.035 g, 80 μmol) were subsequently added to a Schlenk flask filled with 10 mL of toluene and stirred at RT. After 24 h the mixture was filtered and deluted with toluene to reach 40 mL. This solution was used without further purification.

Both methods give a zirconium complex with analogue NMR spectra.

Example 9

Ethylene polymerization experiments (runs 38-48)

The catalytic ethylene polymerization reactions were performed in a 250 mL glass autoclave (Büchi) in semi-batch mode (ethylene was added by replenishing flow to keep the pressure constant). The reactor was ethylene flow controlled and equipped with separate injection systems for toluene, catalyst and co-catalyst. During a polymerization run the pressure and the reactor temperature were kept constant while the ethylene flow was monitored continuously. In a typical semi-batch experiment, the autoclave was evacuated and heated for 1 h at 80° C. prior to use. The reactor was then brought to desired temperature, stirred at 1000 rpm and charged with 150 mL of toluene. After pressurizing with ethylene to reach 2 bar total pressure the autoclave was equilibrated for 10 min. Successive co-catalyst solution (TEA, TMA, TIBA), activator (perfluorophenylborate) and 1 mL of a 0.002 M zirconium pre-catalyst stock solution in toluene was injected, to start the reaction. After the desired reaction time the reactor was vented and the residual aluminium alkyls were destroyed by addition of 50 mL of ethanol. Oligomeric products were collected, stirred for 30 min in acidified ethanol and rinsed with ethanol and acetone on a glass frit. The oligomer was initially dried on air and subsequently in vacuum at 80° C. Oligomeric product was collected by washing the toluene solution with water and removing the solvent under reduced pressure. The oily product was analysed by GC-MS.

A $^1$H NMR spectrum (CDCl$_3$, 26° C.) of the oligomers obtained (46a, *toluene residue) reveled the absence of resonances for olefinic protons in the $^1$H NMR spectrum of the fully saturated oligomeric product proofing that also in the case of guanidinato zirconium as catalyst aluminium terminated oligomers and polymers were formed.

TABLE 4

Ethylene polymerization with Zr catalyst D, trialkylaluminium co-catalyst and perfluorophenylborate activator

| Entry | Precat | Cocat. | Al/Yr | t [min] | $m_{Pol.}$ [g] | Activity [$kg_{PE}mol_{cat}^{-1}h^{-1}bar^{-1}$] | $M_n$ [gmol$^{-1}$] | $M_w/M_n$ |
|---|---|---|---|---|---|---|---|---|
| 38 | D | TEA | 250 | 15 | 1.68 | 1680 | 1300 | 1.9 |
| 39 | D | TEA | 500 | 15 | 1.70 | 1700 | 1140 | 1.5 |
| 40 | D | TIBA | 750 | 15 | 3.54 | 3540 | 1030 | 1.5 |
| 41 | D | TEA | 1000 | 15 | 6.48 | 6480 | 1290 | 1.3 |
| 42 | D | TMA | 1000 | 15 | 0.17 | 170 | 547 | 1.5[b] |
| 43 | D | TIBA | 1000 | 15 | 0.64 | 640 | 2220 | 2.1 |
| 44 | D | TEA | 10000 | 30 | 6.50 | 3270 | 350 | 1.3 |
| 45 | D | TEA | 10000 | 60 | 21.00 | 5250 | 370 | 1.5 |
| 46a[c] | D | TEA | 10000 | 20 | n.d. | n.d. | liquid | n.d. |
| 46b[c] | D | TEA | 10000 | 40 | n.d. | n.d. | 350 | 1.3 |
| 46c[c] | D | TEA | 10000 | 60 | n.d. | n.d. | 380 | 1.4 |
| 46d[c] | D | TEA | 10000 | 80 | n.d. | n.d. | 470 | 1.3 |
| 46e[c] | D | TEA | 10000 | 100 | 35.70 | 5360 | 600 | 1.2 |
| 47 | D | TEA | 20000 | 60 | 21.00 | 5250 | 366 | 1.5 |
| 48[e] | D | TEA | 20000 | 60 | 45.00 | 11250 | 320 | 1.6 |

Precatalyst: 2.0 µmol; ammonium borate: 2.2 µmol [$R_2N(CH_3)H$]$^+$[$B(C_6F_5)_4$]$^-$ (R = $C_{16}H_{33}$ – $C_{18}H_{37}$), Ti/B = 1/1.1; toluene: 150 mL; T = 50° C., p = 2 bar; t = 15 min.
[b] bimodal distribution, major fraction.
[c] continuous sampling every 20 min
[e] T = 80° C.;
TEA: triethylaluminium; TMA: trimethylaluminium; TIBA: triisobutylaluminium, n.d. not determined A GC of oligomers obtained (46a) showed a typical Gaussian distribution of C10 to C32 alcohols peaking at C20. Measurements of the molecular-weight distribution (SEC) of the polymerization runs 45b-e wherein samples were collected each after 20 min revealed a time dependence of the polymer chain. All polymer chains are growing in time, which allows the fully control of the molecular weight by the run-time.

The invention claimed is:

1. Catalyst composition for oligomerizing or polymerizing at least ethylene to obtain oligomers or polymers having a molecular weight (MW) of from 100 to 1000 g/mol comprising
   a) a metal complex as catalyst with the metal being Ti, Zr or Hf having one ligand per metal of formula I:

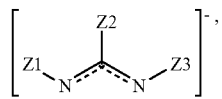

the ligand being bound to the metal, wherein
   Z1, Z2 and Z3 are independently hydrocarbon or heteroatom containing hydrocarbon moieties, wherein the heteroatom, if present for Z1 or Z3, is not directly adjacent to the N-atom and, wherein Z1, Z2, and Z3 independently from each other are optionally linked with one or more of each other,
   b) an organo aluminium compound as co-catalyst, optionally comprising an organo zinc compound as co-catalyst,
   wherein the atomic ratio of the catalyst to the co-catalyst is from 1:10000 to 1:1000000 based on the sum of all Ti, Zr and Hf atoms relative to the sum of all Al and Zn atoms in the composition,
   wherein
   the organo aluminium compound is a C1 to C12 trihydrocarbyl aluminium or a mixture of a C1 to C12 trihydrocarbyl aluminium together with methylaluminoxane, and
   formula I is a guanidate wherein Z2 is NR1R2 with R1 and R2 independently from each other are C1 to C40 hydrocarbon moieties, optionally comprising one or more heteroatoms selected from nitrogen, oxygen or silicon, or
   formula I is an amidinate wherein Z1 and Z3 are a di-ortho substituted aromatic moiety, Z2 is a C1 to C40 hydrocarbon moiety, optionally comprising one or more heteroatoms selected from nitrogen, oxygen or silicon, and
   c) an olefin, the olefin being at least ethylene,
   wherein at least one of Z1 and Z3 is di-ortho-methylphenyl, di-ortho-ethyl phenyl, di-ortho-isopropyl phenyl, or di-ortho-t-butyl phenyl.

2. The composition of claim 1, wherein both of Z1 and Z3 are independently from another di-ortho-methyl phenyl, di-ortho-ethyl phenyl, di-ortho-isopropyl phenyl, or di-ortho-t-butyl phenyl.

3. Catalyst composition for oligomerizing or polymerizing at least ethylene to obtain oligomers or polymers having a molecular weight (MW) of from 100 to 1000 g/mol comprising
   a) a metal complex as catalyst with the metal being Ti, Zr or Hf having one ligand per metal of formula I:

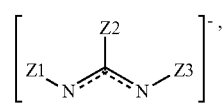

the ligand being bound to the metal, wherein
   Z1, Z2 and Z3 are independently hydrocarbon or heteroatom containing hydrocarbon moieties, wherein the heteroatom, if present for Z1 or Z3, is not directly adjacent to the N-atom and, wherein Z1, Z2, and Z3 independently from each other are optionally linked with one or more of each other,
   b) a co-catalyst being a mixture of an organo aluminium-compound and an organo-zinc compound, wherein the atomic ratio of the catalyst to the co-catalyst is from 1:10000 to 1:1000000 based on the sum of all Ti, Zr and Hf atoms relative to the sum of all Al and Zn atoms in the composition, wherein the organo aluminium compound is a C1 to C12 trihydrocarbyl aluminium or a mixture of a C1 to C12 trihydrocarbyl aluminium together with methylaluminoxane, and formula I is a guanidate wherein Z2 is NR1R2 with R1 and R2 independently from each other are C1 to C40 hydrocarbon moieties, optionally comprising one or more heteroatoms selected from nitrogen, oxygen or silicon, or formula I is an amidinate wherein Z1 and Z3 are a di-ortho substituted aromatic moiety, Z2 is a C1 to C40 hydrocarbon moiety, optionally comprising one or more heteroatoms selected from nitrogen, oxygen or silicon, and c) an olefin, the olefin being at least ethylene.

4. The composition of claim 3, wherein the organo zinc-compound is dihydrocarbyl zinc ZnR$_2$ with R$_2$ being C1-C8, and the atomic ratio of Al to Zn being 100:1 to 1:100.

5. Catalyst composition for oligomerizing or polymerizing at least ethylene to obtain oligomers or polymers having a molecular weight (MW) of from 100 to 1000 g/mol comprising a) a metal complex as catalyst with the metal being Ti, Zr or Hf having one ligand per metal of formula I:

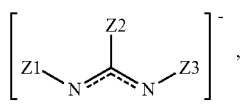

the ligand being bound to the metal, wherein

Z1, Z2 and Z3 are independently hydrocarbon or heteroatom containing hydrocarbon moieties, wherein the heteroatom, if present for Z1 or Z3, is not directly adjacent to the N-atom and, wherein Z1, Z2, and Z3 independently from each other are optionally linked with one or more of each other, b) an organo aluminium compound as co-catalyst, optionally additionally comprising an organo zinc compound as co-catalyst, wherein the atomic ratio of the catalyst to the co-catalyst is from 1:10000 to 1:1000000 based on the sum of all Ti, Zr and Hf atoms relative to the sum of all Al and Zn atoms in the composition, wherein the organo aluminium compound is a C1 to C12 trihydrocarbyl aluminium or a mixture of a C1 to C12 trihydrocarbyl aluminium together with methylaluminoxane, and formula I is a guanidate wherein Z2 is NR1R2 with R1 and R2 independently from each other are C1 to C40 hydrocarbon moieties, optionally comprising one or more heteroatoms selected from nitrogen, oxygen or silicon, and c) an olefin, the olefin being at least ethylene.

6. The composition of claim 5 wherein the metal is Ti or Zr.

7. The composition of claim 5 wherein the metal complex has a structure according to formula III:

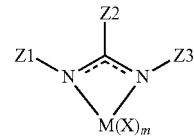

wherein

M is titanium, zirconium or hafnium,

X is halogen; hydrocarbyl; hydride; alkoxide; amide, optionally substituted, and/or tetrahydrofuran, independent for each m;

m is 1, 2, 3 or 4.

8. The composition of claim 5 wherein the metal complex is formed in situ from a transition metal precursor and a ligand precursor.

9. The composition of claim 5 wherein the organo aluminium compound is used together with an organo zinc compound as co-catalyst.

10. The composition of claim 9 wherein the co-catalyst is a mixture of the organo aluminium-compound and the organo zinc-compound, the organo zinc-compound being dihydrocarbyl zinc ZnR$_2$ with R$_2$ being C1-C8, and the atomic ratio of Al to Zn being 100:1 to 1:100.

11. The composition of claim 5 wherein for the guanidate Z1 and Z3 independently from each other are selected from an ortho-substituted aromatic moiety or a di-ortho substituted aromatic moiety.

12. The composition of claim 11 wherein at least one of Z1 and Z3 is, di-ortho-methyl-phenyl, di-ortho-ethyl phenyl, di-ortho-isopropyl phenyl, or di-ortho-t-butyl phenyl.

13. The composition of claim 12, wherein both of Z1 and Z3 are independently from another di-ortho-methyl phenyl, di-ortho-ethyl phenyl, di-ortho-isopropyl phenyl, or di-ortho-t-butyl phenyl.

14. The composition of claim 5 wherein the composition comprises additionally a boron containing compound as activator.

15. The composition of claim 5 wherein the co-catalyst is triethyl aluminium.

16. A process for the production of alcohols or olefins comprising bringing in contact ethylene, or ethylene and propylene with a catalyst composition for oligomerizing or polymerizing at least ethylene to obtain oligomers or polymers having a molecular weight (MW) of from 100 to 1000 g/mol comprising a) a metal complex as catalyst with the metal being Ti, Zr or Hf having one ligand per metal of formula I:

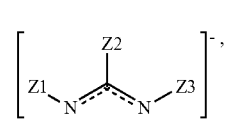

the ligand being bound to the metal, wherein

Z1, Z2 and Z3 are independently hydrocarbon or heteroatom containing hydrocarbon moieties, wherein the heteroatom, if present for Z1 or Z3, is not directly adjacent to the N-atom and, wherein Z1, Z2, and Z3 independently from each other are optionally linked with one or more of each other, b) an organo aluminium compound as co-catalyst, optionally additionally comprising an organo zinc compound as co-catalyst, wherein the atomic ratio of the catalyst to the co-catalyst is from 1:10000 to 1:1000000 based on the sum of all Ti, Zr and Hf atoms relative to the sum of all Al and Zn atoms in the composition,
wherein
the organo aluminium compound is a C1 to C12 trihydrocarbyl aluminium or a mixture of a C1 to C12 trihydrocarbyl aluminium together with methylaluminoxane, and
formula I is a guanidate wherein Z2 is NR1R2 with R1 and R2 independently from each other are C1 to C40 hydrocarbon moieties, optionally comprising one or more heteroatoms selected from nitrogen, oxygen or silicon or
formula I is an amidinate wherein Z1 and Z3 are a di-ortho substituted aromatic moiety, Z2 is a C1 to C40 hydrocarbon moiety, optionally comprising one or more heteroatoms selected from nitrogen, oxygen or silicon, and
c) an olefin, the olefin being at least ethylene;
in order to obtain Al-terminated oligomeric or polymeric hydrocarbons and optionally additionally zinc-terminated oligomeric or polymeric hydrocarbons, wherein a ratio of the Al- terminated oligomeric or polymeric hydrocarbons relative to olefinically terminated hydrocarbons is greater than 10:1, and further comprising
a) eliminating the hydrocarbon to obtain an olefin or
b) converting the aluminium- and optional additional zinc terminated oligomeric or polymeric hydrocarbons with oxygen or a source of oxygen, and hydrolyzing the oxidized oligomers or polymers to yield alcohols.

17. The process as claimed in claim 16 for the production of alcohols wherein the alcohols have a molecular weight (Mw) of from 100 to 1000 g/mol and, optionally independently thereof, wherein more than 80 mol % of the alcohols have a terminal OH group.

18. The process as claimed in claim 16 for the production of olefins, wherein the olefins have a molecular weight (Mw) of from 100 to 1000 g/mol.

19. The process as claimed in claim 16 for the production of alcohols wherein the oxygen or the source of oxygen is a gas comprising oxygen.

20. A metal complex having formula III:

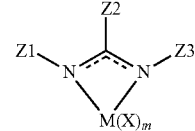

III wherein
Z1 and Z3 are independently from each other an ortho substituted aromatic moiety or a di-ortho substituted aromatic moiety, and
the metal complex is a guanidate with Z2 being NR1R2 and R1 and R2 independently from each other are C1 to C40 hydrocarbon moieties, optionally comprising one or more heteroatoms selected from nitrogen, oxygen, or silicon,
and
Z1, Z2 and Z3 independently from each other are optionally linked with one or more of each other,
wherein
M is titanium, zirconium or hafnium,
X is halogen; hydrocarbyl; hydride; alkoxide; optionally substituted, and/or tetrahydrofuran, independent for each m;
m is 1, 2, 3 or 4.

21. The metal complex of claim 20, wherein at least one of Z1 and Z3 is di-ortho-methyl-pheyl, di-ortho-ethyl phenyl, di-ortho-isopropyl phenyl, or di-ortho-t-butyl phenyl.

* * * * *